(12) United States Patent
Raghuprasad

(10) Patent No.: US 7,727,764 B2
(45) Date of Patent: Jun. 1, 2010

(54) NON-ISOPYCNIC CELL PURIFICATION USING PERCOLL

(76) Inventor: Puthalath Koroth Raghuprasad, 2400 E. 8th St., Odessa, TX (US) 79761

( * ) Notice: Subject to any disclaimer, the term of this patent is extended or adjusted under 35 U.S.C. 154(b) by 639 days.

(21) Appl. No.: 11/616,999

(22) Filed: Dec. 28, 2006

(65) Prior Publication Data

US 2008/0160611 A1 Jul. 3, 2008

(51) Int. Cl.
*C12N 5/071* (2010.01)
*C12N 5/02* (2010.01)

(52) U.S. Cl. .................. 435/378; 435/372; 435/379
(58) Field of Classification Search .............. 435/378, 435/379, 372
See application file for complete search history.

(56) References Cited

U.S. PATENT DOCUMENTS

| | | | |
|---|---|---|---|
| 5,558,834 A | | 9/1996 | Chu et al. |
| 5,811,075 A | * | 9/1998 | Vlassara et al. .............. 424/9.1 |
| 5,876,605 A | | 3/1999 | Kltajima et al. |
| 5,916,743 A | | 6/1999 | Lake et al. |
| 5,985,037 A | | 11/1999 | Dorin et al. |
| 6,221,315 B1 | | 4/2001 | Giesler et al. |
| 6,689,615 B1 | | 2/2004 | Murto et al. |
| 6,982,038 B2 | | 1/2006 | Dolocek et al. |
| 2005/0106552 A1 | | 5/2005 | Ikeda |
| 2006/0011545 A1 | | 1/2006 | Latza |
| 2008/0003224 A1 | * | 1/2008 | Fong et al. ................ 424/139.1 |

FOREIGN PATENT DOCUMENTS

| | | |
|---|---|---|
| GB | 1211942 | 11/1970 |
| JP | 11180876 | 7/1999 |
| JP | 2005066018 | 3/2005 |
| JP | 5052841 | 1/2006 |

OTHER PUBLICATIONS

Percoll Product Information, Pharmacia, Sigma Aldrich, Inc.
Raghuprasad, Puthalath K.; A Rapid Simple Method Of Basophil Purification By Density Centrifugation On Percoll; The Journal Of Immunology; Nov. 1982; vol. 129, No. 5; pp. 2128-2133; The American Association of Immunologists, USA.

* cited by examiner

*Primary Examiner*—Ruth A Davis
(74) *Attorney, Agent, or Firm*—David L. King

(57) ABSTRACT

A method of "non-isopycnic" cell isolation and purification has the steps of adding a sample of blood to a defined volume to a corresponding ratio volume of EDTA solution to produce a volume of anti-coagulated blood; taking a predetermined volume of the anti-coagulated blood and placing it in a first tube containing a selected defined volume of PSS, wherein the selected defined volume of PSS is taken from a group of defined volumes of PSS, as each defined volume of PSS establishes a specific cell type to be purified; centrifuging the tube for a first predetermined time and speed to form a volume of supernatant of plasma/PSS and a bottom sedimented volume of mostly red blood cells; extracting the supernatant to within a proximity of an interface between the sedimented red blood cells and the supernatant; transferring an appropriate, pre-selected volume amount of the supernatant into a second tube holding a defined volume of physiological media; mixing the solutions gently; centrifuging for a second predetermined speed and time; and pouring off the supernatant wherein at the bottom of the tube will be a cell button containing a volume of the selected purified cells in a high percentage and a very small quantity or low percentage of some contaminating non-selected cells. This method is useful in establishing high purity concentrations of selected cells from whole blood such as monocytes, lymphocytes, neutrophils and basophils.

12 Claims, 1 Drawing Sheet

NON-ISOPYCNIC CELL PURIFICATION USING PERCOLL

TECHNICAL FIELD

This invention relates to isolating cells within whole blood samples for later research, tests or studies in the field of medicine and medical research. More particularly to procedures to isolate such cells without damaging them.

BACKGROUND OF THE INVENTION

Medical researchers and scientists have a need to isolate the various cells within whole blood samples in order to conduct tests and experiments.

Human blood for example has red blood cells and white blood cells. Red blood cells deliver oxygen from the lungs to the body tissues. Red blood cells are known as RBCs or erythrocytes (from the Greek erythos "red" and kytos for "hollow"). The white blood cells are produced in bone marrow and help defend the body from infectious disease and foreign materials. White cells derive their name from the fact that after centrifugation of a blood sample, the white cells are found in the Buffy coat, a thin layer of nucleated cells between the sedimented red blood cells and the blood plasma, which is white in color (or sometimes green, if there are large amounts of neutrophils in the sample, which are high in green. This green color is due to neutrophils having MPO, myeloperoxidase).

There are many different types of white blood cells. One primary technique to classify them is to look for the presence of granules, which produces the categories "granulocytes" and "non-granulocytes". Granulocytes are a category of white blood cells, characterized by the fact that all types have differently staining granules in their cytoplasm on light microscopy. These granules are related to lysosomes found in some regular cells and primarily act in the digestion of engulfed invaders. There are three types of granulocytes: neutrophils, basophils, and eosinophils (named according to their staining properties). Non-granulocytes are a category of white blood cells which are characterized by the absence of granules in their cytoplasm. There are two types of non-granulocytes: lymphocytes and monocytes.

These categories can be further broken down into the following cellular types:

Neutrophils deal with defense against bacterial infection and other inflammatory processes and are usually the first responders to bacterial infection; their activity and death in large numbers form pus. Eosinophils primarily deal with parasitic infections and allergic disorders and an increase in them may indicate such. Basophils are chiefly responsible for allergic and antigen response by releasing the chemicals like histamine, causing symptoms of allergies. Lymphocytes are much more common in the lymphatic system. The blood has three types of lymphocytes: B cells: B cells make antibodies that bind to pathogens to enable their destruction. (B cells not only make antibodies that bind to pathogens, but after an attack, some B cells will retain the ability to produce an antibody to serve as a 'memory' system.) T cells: CD4+ (helper) T cells co-ordinate the immune response (they are what become defective in an HIV infection) and are important for defense against intracellular bacteria. CD8+ (cytotoxic) T cells are able to kill virus-infected cells. $\gamma\delta$ T cells possess an alternative T cell receptor as opposed to CD4+ and CD8+ $\alpha\beta$ T cells and share characteristics of helper T cells, cytotoxic T cells and natural killer cells. Natural killer cells: Natural killer (NK) cells are able to kill cells of the body which are not displaying a signal not to kill them, as they have been infected by a virus or have become cancerous. Monocytes share the "vacuum cleaner" (phagocytosis) function of neutrophils, but are much longer lived as they have an additional role: they present pieces of pathogens to T cells so that the pathogens may be recognized and killed, or so that an immune response may be mounted. Monocytes are also known as macrophages after they migrate from the bloodstream and enter tissue.

Since these cells are critical in fighting disease much research and testing is being conducted on these cellular components of blood.

In order to test a patient's blood, a sample is generally taken from a vein. Typically the samples are taken in volumes of 50 cc or more from donors. The whole blood can be placed into a centrifuge and the various blood components can be spun and layered over solutions that separate the cells by different densities such that a skilled technician using great skill and care can isolate certain cell types and withdraw them from the mixture using a pipette so a specific cell type within the whole blood sample can be studied.

This ability to isolate the cell types within blood samples is crucial in medical treatment and research.

The primary goal is naturally to collect as pure a sample of a certain cell type as possible. Along with that goal is another desire or goal to collect a sample that is not chemically altered during the collection process. In both of these goals the present techniques available are either extremely labor intensive and difficult to perform or alternatively if made simpler by the use of nonclonal antibodies, the antibodies can potentially alter the collected cells within a sample or contaminate the otherwise pure cell making it useless for serious research.

It is an objective of the present invention to provide a purification technique that leaves cells undamaged that can be performed using very simple steps requiring far less technical skill.

The technique further employs commonly used materials currently employed by technicians such that the new procedures will be easily adapted but will greatly simplify the task.

SUMMARY OF THE INVENTION

A method of "non-isopycnic" cell isolation and purification has the steps of adding a sample of blood to a defined volume to a corresponding ratio volume of EDTA solution to produce a volume of anti-coagulated blood; taking a predetermined volume of the anti-coagulated blood and placing it in a first tube containing a selected defined volume of PSS, wherein the selected defined volume of PSS is taken from a group of defined volumes of PSS, as each defined volume of PSS establishes a specific cell type to be purified; centrifuging the tube for a first predetermined time and speed to form a volume of supernatant of plasma/PSS and a bottom sedimented volume of mostly red blood cells; extracting the supernatant to within a proximity of an interface between the sedimented red blood cells and the supernatant; transferring an appropriate, preselected volume amount of the supernatant into a second tube holding a defined volume of physiological media; mixing the solutions gently; centrifuging for a second predetermined speed and time; and pouring off the supernatant wherein at the bottom of the tube will be a cell button containing a volume of the selected purified cells in a high percentage and a very small quantity or low percentage of some contaminating non-selecting cells.

This method is useful in establishing high purity concentrations of selected cells from whole blood such as monocytes, lymphocytes, neutrophils and basophils.

BRIEF DESCRIPTION OF THE DRAWINGS

The invention will be described by way of example and with reference to the accompanying drawings in which.

DEFINITIONS

Anti-coagulated blood as used herein means 10 ml of blood to which 1 ml of 001M EDTA has been added.

EDTA: Ethylenediaminetetraacetic acid

Isopycnic means a process by which cells are captured between two ranges of densities by cells having a density within these two ranges.

PSS: Percoll Stock Solution

RHAE: RPMI, HEPES, HSA and EDTA

HSA: Human Serum Albumin

RPMI: RPMI medium 1640 is a media manufactured by Gibco/Invitrogen Corp. containing micronutrients and minerals.

HEPES: HEPES buffer solution is a commercially available solution.

DETAILED DESCRIPTION OF THE INVENTION

The following is a description of a "non-isopycnic" cell purification procedure that is suitable for any laboratory conducting research requiring cell isolation within blood samples to be performed. The procedure is particularly useful in isolating neutrophils, lymphocytes, and monocytes requiring no screening of the donors. For basophil purification, as the number of these cells in the peripheral blood is very low (usually less than 1 percent), it is useful to screen donors and check the peripheral blood basophil count. Those with basophil counts above 2 percent are ideal. Studies have found that these subjects also have higher degrees of allergies. The basophil purification is unique in that it needs a third step process to properly purify and isolate the cells from a whole blood sample, whereas the other cell types need only two steps to achieve isolation and purification of the cell samples.

A primary advantage of the procedure proposed in this patent application is that the cells do not have to be layered or isolated, which is a common practice using Percoll™ wherein the technician must very carefully not disturb the layers to insure that only the cells within a particular density matrix or layer are pulled up using a pipette and from those layered samples the technician is able to provide a purified or isolated cell sample which has been preselected. While these known density layering techniques are available, they are performed with great degrees of difficulty, often requiring a repeat test procedure which is costly and sometimes requires additional sampling from the donor. An alternative to using the layered technique as described in the Percoll™ procedures is to use chemicals or other materials such as monoclonal antibodies that can potentially affect the cells, in other words the addition of such chemicals can adversely affect the cell quality and therefore may impede any research being conducted on a specific cell type as the cell has been altered by the addition of such chemicals. Therefore an objective of the present inventive procedure is to avoid the addition of any such chemicals that can affect the purity of the sample.

Figure 1:
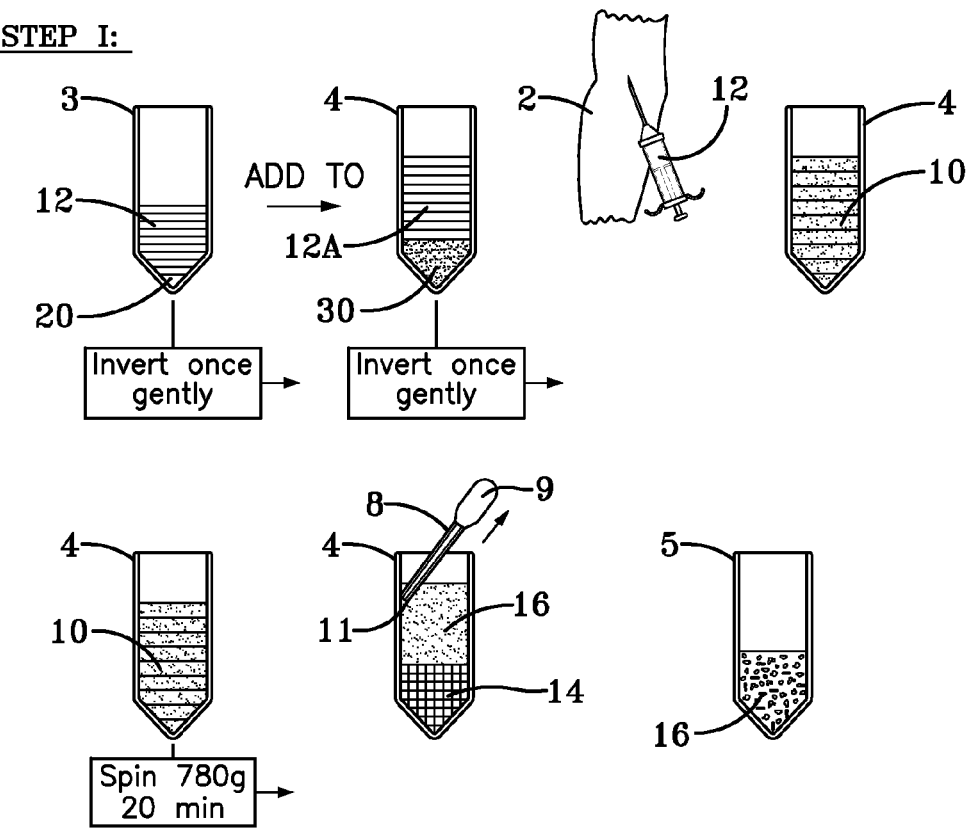
FIG. 1 is a schematic view of the overall procedure.
Figure 1:
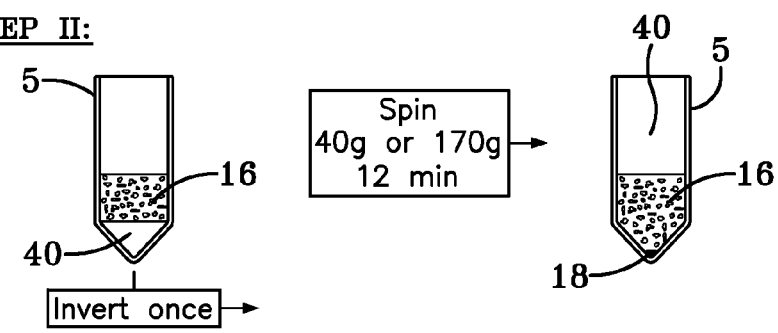
Figure 1:
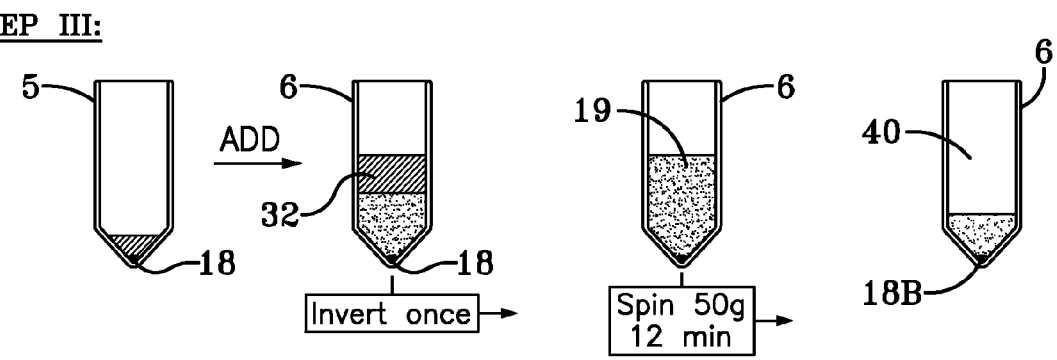

The basic technique requires as first shown schematically in FIG. 1, starts by collecting blood wherein a defined volume of blood 12 is drawn through a suitable peripheral vein of a donor 2 and transferred to a 50 ml plastic initial preparation tube 3 that already has the appropriate volume 20 of EDTA solution (this is 1 ml of 0.1 M EDTA for each 10 ml of blood).

By gently inverting the preparation tube 3 once only so as not to stir or shake violently, as this tends to disturb the cells, the combination of the blood and EDTA solution can be mixed such that the cells do not change their density. A defined volume of this anti-coagulated blood 12A is then removed from the 50 ml initial preparation tube 3 using a pipette 8 and added gently to a first tube or set of tubes 4 each containing the defined volume 30 of PSS which is the appropriate volume of PSS dependent on the type of cell to be purified. Each cell type will have a specific amount of PSS that needs to be added dependent on the type of cells to be isolated. Then the first tube or set of tubes containing a mixture 10 of anti-coagulated blood 12A and the volume 30 of PSS are placed in the centrifuge (not illustrated) in opposite rows to balance; (alternatively dummy tubes containing the same amount of water can be employed to balance the centrifuge) thereafter running the centrifuge at a predetermined speed and a predetermined length of time. After centrifuging, each first tube 4 is removed carefully in order not to disturb the now separate layers of different elements of blood. Using a plastic transfer pipette 8 the technician carefully extracts the supernatant 16 down to approximately within 5 to 10 mm of the interface between the sedimented red blood cells 14 and the plasma/PSS supernatant 16. The technician must be careful not to disturb the well defined interface between the plasma/PSS 16 and the red blood cells 14 in the bottom of the tube 4. Preferably, the bulb 9 of the transfer pipette 8 is squeezed before advancing the tip 11 along the inside of the first tube or tubes 4 and into the supernatant 16 and then the bulb 9 is gently released while leaving the tip 11 in contact with the wall of the tube 4. The technician then transfers this supernatant 16 into a clean second 50 ml plastic tube 5 preparing for the second step of the required procedure.

In the second step of this procedure a defined volume 40 of physiological media is placed in the 50 ml conical plastic second tube or tubes 5. The physiological media used is a combination of RPMI 1640 media, 25 mM HEPES, Human Serum Albumin and EDTA, collectively referred to hereafter as RHAE by the inventor. To this is added the appropriate volume of the supernatant 16. The volume of the supernatant 16 added is dependent on the type of cell to be isolated. Again the technician will simply invert the second tube or tubes 5 once to mix the solution and then spin at the appropriate speed and length of time of the cells to be isolated using the centrifuge. Once centrifuged the technician pours off the supernatant and at the bottom of the tube 5 will be a cell button 18 now containing a purified cell type and some contaminating cells.

In the case of isolating basophils the cells are then taken through another step. The technician takes clean third tubes, preferably 5 ml plastic tubes 6 containing a defined volume 32 of 0.575 ml PSS and 1.0 ml of the cell suspension obtained after step 2. Again by a gentle single inversion of the third tube 6 a mixture 19 results and this mixture 19 is then spun in a centrifuge at an appropriate speed, preferably 50 g for a length of time of approximately 12 minutes. A cell button 18B is then formed in the bottom of the tube 6 which will contain purified basophils with contaminating cells which are usually lymphocyte cells. In this procedure the cell purity of basophil cells is achieved in the 50 to 80 percent range.

FIG. 1 illustrates a master schematic for all the cells and shows the obtaining of the blood 12 from donors 2 and anti-coagulating it, the removing of the red blood cells and unwanted heavy white blood cells in step one and the removing of the main contaminating cells in the supernatant achieved in step 2 and in step 3 shows the additional step required for removing the remaining contaminants to achieve a purified basophil cell volume.

With regards to the above described procedure, each cell type has a specific amount or volume required of different solutions and spin components to achieve a proper isolation and purification of the desired cell types.

For example, monocytes in step one will have 20 ml of anti-coagulated blood, added to 5 ml of PSS which has been pre-placed in the first tube prior to adding the anti-coagulated blood samples. The technician inverts once as previously noted and then spins the first tubes at a speed of 780 g for 20 minutes, preferably the first tubes are 50 ml conical bottomed plastic tubes from which the technician can collect the supernatant using a plastic transfer pipette leaving approximately 1 cm of the supernatant from the interface with the sediment of red blood cells and heavy white blood cells. Then with regards to step 2 a second 50 ml conical bottomed plastic tube or tubes each containing 5 ml of RHAE has 7 ml of the supernatant added. The technician will then invert once to gently mix and then spin the second tube or tubes at 40 g for 7 minutes. The technician will then discard the supernatant from this and resuspend the cell button in 1 ml of RHAE for each tube. This will contain monocytes of high purity with lymphocytes as the occasional contaminant. This purity level generally is 95% or greater.

With regard to lymphocytes, a 50 ml conical bottomed plastic first tube or tubes have 10.25 ml of PSS placed in it to which the technician will add 20 ml of anti-coagulated blood to each first tube or tubes. The technician will invert once to gently mix, spin at 780 g for 20 minutes and then collect the supernatant using a plastic transfer pipette leaving approximately 1 cm of the supernatant adjacent to the interface with the sediment. Then in step 2 a second 50 ml conical bottomed plastic tube or tubes each already containing 2 ml of RHAE has added to it 7 ml of the supernatant and is spun at 170 g for 12 minutes. Thereafter the technician pours off the supernatant and collects the cell button in 1 ml of RHAE; this will result in a purified cell volume predominately of lymphocytes at a 95% concentration with a rare contaminating monocyte.

With regard to neutrophils in step one a 50 ml conical bottomed plastic first tube or tubes each containing 20 ml of PSS has 20 ml of anti-coagulated blood. The technician will then invert once to mix, spin at 780 g for 20 minutes and collect the supernatant leaving 1 cm of above the level of the interface from the sediment.

With regard to step 2 a second 50 ml conical bottomed plastic tube or tubes each containing 6 ml RHAE has added to it 15 ml of the supernatant and is inverted once to mix the solution and thereafter spun at 170 g for 12 minutes. Thereafter the technician discards the supernatant and will collect the cell button in 1 ml of RHAE. This will contain almost entirely pure neutrophils.

As can be seen, with each of these cell types the procedure is fundamentally identical with the exception of the volume of solutions to be added and the volumes of supernatants. These techniques have been tested and evaluated over a long period of time and the reliability has been well established such that a high confidence level can be achieved when used to isolate monocytes, lymphocytes and neutrophils.

With regard to basophils an additional step is required. In using the procedure to isolate basophils the technician will start with a first 50 ml conical bottomed plastic tube or tubes and add 10.25 ml PSS to each and to this the technician will then add 20 ml of anti-coagulated blood. The technician inverts once gently to mix and then will spin in a centrifuge at 780 g for 20 minutes. After that the technician collects 7 ml of the supernatant from each first tube carefully without disturbing the interface between the plasma/PSS layer in the sedimented RBC layer. In step 2 the technician takes a second 50 ml conical bottomed plastic tube or tubes to which is added 0.60 ml of RHAE in each tube and to this adds to each second tube 7 ml of the above supernatant. The technician then inverts the mixture to mix gently and then spins at 170 g for 12 minutes. Thereafter the technician pours off the supernatant and collects the cell button in 1 ml of RHAE.

In a third step the technician takes a third 5 ml plastic tube or tubes and adds 0.575 ml PSS and to this adds 1 ml of cell suspension from step 2. The technician then inverts the third tube or tubes once to mix and then spins at 50 g for 12 minutes. After which the technician pours off the supernatant and collects the cell button in 1 ml of RHAE. This volume of cells will contain basophils in high purity in the range of 50-80 percent.

As can be seen each of the procedures is almost identical which provides a rather uniform procedure for isolating cell types from blood samples. As such the technique can be basically accomplished in a rather routine fashion which is very simple and is less likely to create errors. A most beneficial feature is that the cells are purified without the addition of any chemicals thus ensuring that the sample will be purified cells of the highest quality. By avoiding the normal layering required using standard Percoll ™ technique the present procedure greatly simplifies and reduces the amount of errors that can occur during a transfer and pipetting of the cell layers. As such it has been determined that the laboratory can achieve very high quality results without the need of tremendous skill on the part of the technician. The only required skill level is that the technician be able to adequately measure the volumes required and to achieve the proper timing on all the centrifuges. These are rather routine requirements for a technician and greatly improves the reliability of the system.

Each of the systems described above for isolating a specific cell type can be accomplished using the basic equipment within a typical laboratory. For the above procedures the following materials were used as provided in the list below.

Materials:
  Centrifuge: Marathon 21K/R Refrigerated centrifuge, Fisher Scientific
  Cytocentrifuge: Cytospin 2, Shandon. Cytofunnels were provided by the company
  Coulter Counter: Z1 (Becton Coulter Corporation)
  Stainer: Midas II, Harleco EM Sciences
  Stain: Wright Geimsa stain, E.K. Industries, Joliet, Il 60432
  Pipettes: 1. 10 ml serological plastic pipettes (Falcon, Becton Dickinson)
    2. "Elkay Liquipette" plastic transfer pipettes (Tyco/Healthcare)
  Tubes: 1. 50 ml conical-bottomed plastic tubes (Falcon, Becton Dickenson)
    2. 5 ml round bottom plastic tubes (Falcon, Becton Dickinson)

This list is provided only as exemplary as it is understood the procedures could be achieved using alternative equipment types or size from various other manufacturers.

In addition, the technician is required to prepare the necessary reagents, the following list of reagents were prepared as provided below.

Preparation of Reagents:
  Percoll Stock Solution (PSS): Add 9.0 ml 1M NaCl to 100 ml glass volumetric flask. To this add 0.40 ml of 1 M HCl. Mix by inverting and to this mixture add commercial Percoll solution (Amersham Biosciences, Uppsala, Sweden). Mix thoroughly by inverting several times, then store in refrigerator at 4° C. until used, in 100 ml graduated cylinder.

RHAE: (RPMI 1640 media with 25 mM HEPES (Invitrogen Corp, Grand Island, N.Y.), Human Serum Albumin and EDTA): to each 100 ml bottle of RPMI 1640 with 25 mM HEPES buffer add 1 ml Human Serum Albumin and 1 ml of 0.1 M EDTA and to this mixture add 1 M NaOH to make pH 7.40±0.05

Human Serum Albumin (HAS): (Sigma-Aldrich, St. Louis, Mo.) Add 1.5 g of lyophilized HSA to a 100 ml graduated cylinder and add to it distilled water to 100 ml. This solution is then Millipore-filtered (25 microns) and divided into 1 ml aliquots. Store in sterile 5 ml plastic tubes and keep frozen until use.

EDTA: (Ethylenediaminetetraacetic acid, Sigma-Aldrich) Weigh out 7.3 g of EDTA powder into a 250 ml beaker. Add 200 ml of reagent grade water. The pH is then adjusted to 7.40 by adding, drop-wise 1M NaOH. This is then stored in a refrigerator at 4° C. until use.

It is believed that all of these reagents and the necessary equipment could be provided in kits wherein the 50 ml tubes could be prepared in such a fashion that the technicians would simply take tubes that are provided and simply add the anti-coagulated blood samples as described above. In other words, prepared tubes with a certain amount of PSS added can be provided in a kit form such that the technician simply has to add the right amount of anti-coagulated blood sample and centrifuge as outlined in the procedure. Thus greatly enhancing the productivity of the lab generally. These kits of prepared tubes for non-isopycnic cell purification could include one or more kits selected from a group of kits including a kit for monocytes, a kit for lymphocytes, a kit for neutrophils and a kit for basophils, wherein each kit includes a selected defined volume of PSS contained in each of one or more first tubes and a selected defined volume of physiological media in each of one or more second tubes. The kit for basophils further would include one or more third tube containing a selected defined volume of PSS, each third tube being a 5 ml round bottom plastic tube. Preferably, each of the first or second tubes is a 50 ml conical bottom plastic tube.

The kit for monocytes cells has 5 ml of PSS in each first tube and 5 ml of RHAE in each second tube. While the kit for lymphocytes cells has 10.25 ml of PSS in each first tube and 2 ml of RHAE in each second tube. The kit for neutrophils cells has 20 ml of PSS in each first tube and 6 ml of RHAE in each second tube. The kit for basophils cells has 10.25 ml of PSS in each first tube and 0.6 ml of RHAE in each second tube and has 0.575 ml of PSS in each third tube.

The above described procedure as shown provides samples of purified cells having a purity of typically greater than 90% with less than 10% of contaminants, in most cases greater than 95% purity except for the isolation of the basophil cells. In the above referenced process for cell purification the blood samples were selected from human male donors. It is appreciated that the selected volumes of PSS and RHAE as well as the amount of anti-coagulated blood used for female human donors may vary from males donors and therefore the selected defined volumes may change only for step one, however the basic procedure as described will remain the same for the second/third steps.

While applicants have only provided the procedure for 4 types of cells it is recognized that additional cell types can be isolated using the technique; however, the proper volumes and amounts of time and speeds required for centrifuging need to be determined through further experimenting and testing.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

I claim:

1. A two step method of non-isopycnic cell isolation and purification comprises the steps of:
   initiating a first step of cell isolation by adding a sample of blood of a defined volume to an initial preparation tube having a corresponding ratio volume of ethylenediaminetetraacetic acid, EDTA solution to produce a volume of anti-coagulated blood;
   mixing gently by sealing the end of the preparation tube, inverting the preparation tube once so as not to shake or stir violently to mix the combination of blood and EDTA solution while avoiding changing the cell density;
   taking a predetermined volume of the anti-coagulated blood from the initial preparation tube and gently placing in a first tube containing a selected defined volume of percoll stock solution, PSS, wherein the selected defined volume of PSS is taken from a group of defined volumes of PSS, each defined volume of PSS establishes a specific cell type to be isolated and purified;
   mix gently by sealing the end and inverting the first tube once;
   centrifuging the tube for a first predetermined time and predetermined speed in the absence of isopycnic cell layering to form a mixed volume of supernatant of plasma/PSS and a lower bottom sedimented volume of red blood cells;
   extracting the supernatant of plasma/PSS containing the cell type to be isolated to within 5 mm to 10 mm of an interface between the sedimented red blood cells and the supernatant for transfer into a second tube completing the first step of cell isolation;
   initiating a second step of cell isolation by transferring an appropriate pre-selected volumetric amount of the supernatant into the second tube holding a defined volume of physiological media to form a solution of the supernatant of plasma/PSS and the physiological media;
   mixing the solutions gently by sealing the end of the second tube and inverting the second tube once;
   centrifuging for a second predetermined speed and time in the absence of isopycnic cell layering; and
   pouring off the supernatant and at the bottom of the tube will be a cell button containing a quantity of the selected purified cells in a high percentage and a low percentage of some contaminating non selected cells, the selected purified cells being purified in the absence of chemical washing and normal cell layering thereby completing the non-isopycnic cell isolation in two steps.

2. The method of claim 1 wherein the percentage of purified cells is greater than 90% and the percentage of contaminated non selected cells is less than 10% of the total volume of the cell button.

3. The method of claim 1 further comprises the step of collecting the sample of blood from a suitable peripheral vein of the donor.

4. The method of claim 1 wherein the step of adding a sample of blood to a defined volume of EDTA to produce a volume of anti-coagulated blood, further comprises transferring the blood into a 50 ml plastic tube holding EDTA solution in the amount of 1 ml per each 10 ml's of blood and gently mixing only once in the absence of any stirring or violent shaking which could affect cell density.

5. The method of claim 1 wherein the step of placing the anti-coagulated blood in a first tube further comprises the steps of using a pipette to remove the anti-coagulated blood and adding gently to the first tube.

6. The method of claim 1 wherein the step of centrifuging for a first predetermined speed and time further comprises balancing the centrifuge with dummy tubes holding water.

7. The method of claim 1 wherein the step of extracting the supernatant further comprises using a transfer pipette to carefully extract the supernatant to within 5 to 10 mm of the interface between the sedimented red blood cells and the supernatant of plasma/PSS.

8. The method of claim 7 further comprises the steps of squeezing the bulb of the transfer pipette before advancing the tip of the pipette along the inside wall of the tube immersing into the supernatant and then gently releasing the bulb to draw the fluid into the pipette while keeping the tip in contact with the tube wall so as not to disturb the layers; and then transferring the filled pipette into a clean 50 ml second tube holding a defined volume of physiological media containing RPMI 1640 media, 25 mM HEPES, Human Serum Albumin and EDTA, collectively referred to as RHAE.

9. The method of claim 1 wherein the cell being isolated and purified is monocytes and the steps further comprise:
   preparing a first tube of 50 ml volume and having a conical bottom with 5 ml of PSS;
   placing the predetermined volume of anti-coagulated blood in the amount of 20 ml;
   sealing the end of the tube inverting once gently to mix;
   centrifuging at 780 g for 20 minutes;
   collecting the supernatant using a transfer pipette, leaving about 1 cm of supernatant from the interface with the sediment;
   transferring 7 ml of supernatant into a second tube of 50 ml volume having a conical bottom containing 5 ml of physiological media containing RPMI 1640 media, 25 mM HEPES, Human Serum Albumin and EDTA, collectively referred to as RHAE, sealing the end of the tube, inverting to gently mix and centrifuging at 40 g for 7 min;
   discarding the supernatant; and
   resuspending the "cell button" in 1 ml of RHAE to result in a suspension of greater than 95 percent monocytes and less than 5 percent lymphocytes as a contaminant.

10. The method of claim 1 wherein the cell being isolated and purified is lymphocytes and the steps further comprise:
    preparing a first tube of 50 ml volume and having a conical bottom with 10.25 ml PSS;
    placing the predetermined volume of anti-coagulated blood in the amount of 20 ml;
    sealing the end of the tube inverting once gently to mix;
    centrifuging at 780 g for 20 minutes;
    collecting the supernatant using a transfer pipette, leaving about 1 cm of supernatant adjacent to the interface with the sediment;
    transferring 7 ml of supernatant into a second tube of 50 ml volume having a conical bottom containing 2 ml of RHAE, sealing the end of the tube, inverting to gently mix and centrifuging at 170 g for 12 min;
    discarding the supernatant; and
    resuspending the "cell button" in 1 ml of RHAE to result in a suspension of greater than 95 percent isolated and purified lymphocytes with a rare contaminating monocyte.

11. The method of claim 1 wherein the cell being isolated and purified is neutrophils and the steps further comprise:
    preparing a first tube of 50 ml volume and having a conical bottom with 20 ml of PSS;
    placing the predetermined volume of anti-coagulated blood in the amount of 20 ml;
    sealing the end of the tube inverting once gently to mix;
    centrifuging at 780 g for 20 minutes;
    collecting the supernatant using a transfer pipette, leaving about 1 cm of supernatant from the interface with the sediment;
    transferring 15 ml of supernatant into a second tube of 50 ml volume having a conical bottom containing 6 ml of RHAE, sealing the end of the tube, inverting to gently mix and centrifuging at 170 g for 12 min;
    discarding the supernatant; and
    resuspending the "cell button" in 1 ml of RHAE to result in a suspension of greater than 95 percent isolated and purified neutrophils.

12. The method of claim 1 wherein the cell being isolated and purified is basophils and the steps further comprise:
    preparing a first tube of 50 ml volume and having a conical bottom with 10.25 ml of PSS;
    placing the predetermined volume of anti-coagulated blood in the amount of 20 ml;
    sealing the end of the tube inverting once gently to mix;
    centrifuging at 780 g for 20 minutes;
    collecting 7 ml of the supernatant;
    transferring 7 ml of supernatant into a second tube of 50 ml volume having a conical bottom containing 0.6 ml of RHAE, sealing the end of the tube, inverting to gently mix and centrifuging at 170 g for 7 min;
    discarding the supernatant and resuspending the "cell button" in 1 ml of RHAE;
    transferring 1 ml of the cell suspension into a third tube of 5 ml volume with a conical bottom containing 0.575 ml PSS, sealing the end of the tube and inverting to mix and centrifuging at 50 g for 12 min;
    discarding this supernatant and resuspending and collecting the cell button in 1 ml of RHAE to result in a suspension of basophils cells in a high purity between 50 percent and 80 percent.

* * * * *